United States Patent
Bund et al.

(10) Patent No.: US 10,907,141 B2
(45) Date of Patent: Feb. 2, 2021

(54) REP PROTEIN FOR USE IN A DIAGNOSTIC ASSAY

(71) Applicant: Deutsches Krebsforschungszentrum, Heidelberg (DE)

(72) Inventors: Timo Bund, Dossenheim (DE); Ethel-Michele De Villiers-Zur Hausen, Waldmichelbach (DE); Harald Zur Hausen, Waldmichelbach (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 16/730,473

(22) Filed: Dec. 30, 2019

(65) Prior Publication Data

US 2020/0123520 A1   Apr. 23, 2020

Related U.S. Application Data

(63) Continuation of application No. PCT/ED2018/068118, filed on Jul. 4, 2018.

(30) Foreign Application Priority Data

Jul. 7, 2017   (EP) ..................................... 17180235

(51) Int. Cl.
    *C12N 9/50*      (2006.01)
    *G01N 33/53*     (2006.01)
    *G01N 33/535*    (2006.01)
    *G01N 33/543*    (2006.01)
    *G01N 33/577*    (2006.01)

(52) U.S. Cl.
    CPC ........... *C12N 9/506* (2013.01); *G01N 33/535* (2013.01); *G01N 33/5306* (2013.01); *G01N 33/54333* (2013.01); *G01N 33/577* (2013.01); *C12Y 306/01003* (2013.01); *G01N 2333/435* (2013.01); *G01N 2333/9513* (2013.01)

(58) Field of Classification Search
    None
    See application file for complete search history.

(56) References Cited

FOREIGN PATENT DOCUMENTS

EP      2966176 A1    1/2016

OTHER PUBLICATIONS

Sotirios Botsios, et al., "CJD and Scrapie Require Agent-Associated Nucleic Acids for Infection", Journal of Cellular Biochemistry vol. 117, No. 8, Aug. 1, 2016, p. 1947-1958.
Toshisangba Longkumer, et al., "Acinetobacter phage genome is similar to Sphinx 2.36, the circular DNA copurified with TSE infected particles", Scientific Reports, vol. 3, No. 1, Jul. 19, 2013, 10 pages.
Laura Molina-García, et al., "Functional amyloids as inhibitors of plasmid DNA replication", Scientific Reports, vol. 6, No. 1, May 5, 2016, 8 pages.
Corinna Whitley, et al., "Novel Replication-Competent Circular DNA Molecules from Healthy Cattle Serum and Milk and Multiple Sclerosis-Affected Human Brain Tissue", Genome Announcements, Aug. 28, 2014, vol. 2, No. 4, 2 pages.
International Search Report dated Aug. 10, 2018 issued in PCT/EP2018/068118.

*Primary Examiner* — John D Ulm
(74) *Attorney, Agent, or Firm* — Perkins Coie LLP; Viola Kung

(57) ABSTRACT

The present invention concerns a DNA-replication-associated (Rep) protein comprising an amino acid sequence as depicted in SEQ ID NO: 11 or 12; (b) a fragment of SEQ ID NOs:11 or 12 which is capable of binding an anti-Rep antibody specific for a protein having the amino acid sequence of SEQ ID NOs: 11 or 12; or (c) an amino acid sequence having a 90% or more homology to the amino acid sequence of (a) or (b) and is capable of binding an anti-Rep antibody specific for a protein having an amino acid sequence of SEQ ID NOs:11 or 12. The present invention further concerns a method of diagnosing MS or a predisposition for MS and a kit for use in such methods.

10 Claims, 6 Drawing Sheets

Specification includes a Sequence Listing.

SEQUENCE LISTING

<160> NUMBER OF SEQ ID NOS: 12

<210> SEQ ID NO 1
<211> LENGTH: 324
<212> TYPE: PRT
<213> ORGANISM: homo sapiens

```
<400> SEQUENCE: 1

Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Leu Ala Ile Ile Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
                100                 105                 110

Ile Phe Ala Pro Ala Val Val Pro Leu Ile Thr Arg Leu Glu Glu Gln
                115                 120                 125

Phe Thr Gln Tyr Asp Ile Glu Gln Ile Ser Gly Leu Ser Ser Ala Tyr
                130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Arg Val Ile Glu
                180                 185                 190

Leu Ala Leu Lys Gln Ile Asn Glu His Thr Asp Ile Thr Ala Ser Tyr
                195                 200                 205

Glu Gln His Lys Lys Gly Arg Val Ile Thr Gly Phe Ser Phe Lys Phe
                210                 215                 220

Lys His Lys Lys Gln Asn Ser Asp Lys Thr Pro Lys Asn Ser Asp Ser
225                 230                 235                 240

Ser Pro Arg Ile Val Lys His Ser Gln Ile Pro Thr Asn Ile Val Lys
                245                 250                 255

Gln Pro Glu Asn Ala Lys Met Ser Asp Leu Glu His Arg Ala Ser Arg
                260                 265                 270

Val Thr Gly Glu Ile Met Arg Asn Arg Leu Ser Asp Arg Phe Lys Gln
                275                 280                 285

Gly Asp Glu Ser Ala Ile Asp Met Met Lys Arg Ile Gln Ser Glu Ile
                290                 295                 300

Ile Thr Asp Ala Ile Ala Asp Gln Trp Glu Ser Lys Leu Glu Glu Phe
305                 310                 315                 320

Gly Val Val Phe

<210> SEQ ID NO 2
<211> LENGTH: 18
<212> TYPE: PRT
<213> ORGANISM: homo sapiens

<400> SEQUENCE: 2

Glu Ala Arg Glu Thr Gly Lys Gly Ile Asn Ala Asn Asp Pro Leu Thr
1               5                   10                  15

Val His
```

```
<210> SEQ ID NO 3
<211> LENGTH: 21
<212> TYPE: PRT
<213> ORGANISM: homo sapiens

<400> SEQUENCE: 3

Lys Gln Ile Asn Glu His Thr Asp Ile Thr Ala Ser Tyr Glu Gln His
1               5                   10                  15

Lys Lys Gly Arg Thr
            20

<210> SEQ ID NO 4
<211> LENGTH: 8
<212> TYPE: PRT
<213> ORGANISM: artificial sequence
<220> FEATURE:
<223> OTHER INFORMATION: His-Tag

<400> SEQUENCE: 4

Gly Ala His His His His His His
1               5

<210> SEQ ID NO 5
<211> LENGTH: 11
<212> TYPE: PRT
<213> ORGANISM: artificial sequence
<220> FEATURE:
<223> OTHER INFORMATION: T7 Tag

<400> SEQUENCE: 5

Met Ala Ser Met Thr Gly Gly Gln Gln Met Gly
1               5                   10

<210> SEQ ID NO 6
<211> LENGTH: 8
<212> TYPE: PRT
<213> ORGANISM: artificial sequence
<220> FEATURE:
<223> OTHER INFORMATION: Flag Tag

<400> SEQUENCE: 6

Asp Tyr Lys Asp Asp Asp Asp Lys
1               5

<210> SEQ ID NO 7
<211> LENGTH: 8
<212> TYPE: PRT
<213> ORGANISM: artificial sequence
<220> FEATURE:
<223> OTHER INFORMATION: Strep II Tag

<400> SEQUENCE: 7

Trp Ser His Pro Gln Phe Glu Lys
1               5

<210> SEQ ID NO 8
<211> LENGTH: 319
<212> TYPE: PRT
<213> ORGANISM: homo sapiens

<400> SEQUENCE: 8

Met Ser Lys Leu Val Val Lys Asp Asn Ala Leu Met Asn Ala Ser Tyr
1               5                   10                  15

Asn Leu Asp Leu Val Glu Gln Arg Leu Ile Leu Leu Ala Ile Ile Glu
            20                  25                  30
```

```
Ala Arg Glu Ser Gly Lys Gly Ile Asn Ala Asn Asp Pro Leu Thr Val
         35                  40                  45

His Ala Glu Ser Tyr Ile Asn Gln Phe Gly Val His Arg Val Thr Ala
 50                  55                  60

Tyr Gln Ala Leu Lys Asp Ala Cys Asp Asn Leu Phe Ala Arg Gln Phe
 65                  70                  75                  80

Ser Tyr Gln Ser Lys Ser Glu Lys Gly Asn Ile Gln Asn His Arg Ser
                 85                  90                  95

Arg Trp Val Ser Glu Ile Ile Tyr Ile Asp Thr Glu Ala Thr Val Lys
                100                 105                 110

Ile Ile Phe Ala Pro Ala Ile Val Pro Leu Ile Thr Arg Leu Glu Glu
                115                 120                 125

Gln Phe Thr Lys Tyr Asp Ile Glu Gln Ile Ser Asp Leu Ser Ser Ala
130                 135                 140

Tyr Ala Ile Arg Leu Tyr Glu Leu Leu Ile Cys Trp Arg Ser Thr Gly
145                 150                 155                 160

Lys Thr Pro Ile Ile Gly Leu Gly Glu Phe Arg Asn Arg Val Gly Val
                165                 170                 175

Leu Asp Ser Glu Tyr His Arg Ile Ala His Leu Lys Glu Arg Val Ile
                180                 185                 190

Glu His Ser Ile Lys Gln Ile Asn Glu His Thr Asp Ile Thr Ala Thr
                195                 200                 205

Tyr Glu Gln His Lys Lys Gly Arg Thr Ile Thr Gly Phe Ser Phe Lys
                210                 215                 220

Phe Lys Gln Lys Lys Pro Lys Gln Ala Glu Ile Ala Thr Glu Thr Pro
225                 230                 235                 240

Lys Thr Ala Thr Asn Asp Pro Asp Thr Lys Pro Leu Thr Glu Pro
                245                 250                 255

Gln Ile Ala Lys Tyr Ser Met Ile Leu Cys Lys Leu Gly Ser Ile Ser
                260                 265                 270

Asp Leu Ser Asn Phe Pro Asp Tyr Pro Ala Phe Ala Asn Trp Ile Gly
                275                 280                 285

Asn Ile Leu Arg Asn Pro Glu Lys Ala Asp Glu Gln Ile Ala Lys Arg
                290                 295                 300

Ile Phe Thr Ala Leu Lys Thr Glu Thr Asp Tyr Ser Lys Lys Asn
305                 310                 315

<210> SEQ ID NO 9
<211> LENGTH: 7
<212> TYPE: PRT
<213> ORGANISM: homo sapiens

<400> SEQUENCE: 9

Asn Arg Leu Ser Asp Arg Phe
1               5

<210> SEQ ID NO 10
<211> LENGTH: 999
<212> TYPE: DNA
<213> ORGANISM: artificial sequence
<220> FEATURE:
<223> OTHER INFORMATION: MSBI1 Rep 27/154E mutant

<400> SEQUENCE: 10
atgagcgacc tgatcgtgaa agacaatgcc ctgatgaacg cctcctacaa cctggcactg      60
gtcgaacaga gactgattga gctggctatc atcgaggcaa gggagaccgg caagggcatc    120
```

```
aacgccaatg accccctgac agtgcacgcc agctcctaca tcaaccagtt taatgtggag    180
cgccacaccg cctatcaggc cctgaaggac gcctgcaagg atctgtttgc ccggcagttc    240
agctaccagg agaagcggga gagaggcagg atcaacatca aagcagatg ggtgtcccag    300 atcggctata tggacgatac cgccacagtg gagatcatct ttgcaccagc agtggtgcct    360
ctgatcacca ggctggagga gcagttcaca cagtacgaca tcgagcagat ctccggactg    420
tctagcgcct acgccgtgcg catgtatgag ctgctgatcg agtggcggtc taccggcaag    480
acacctatca tcgagctgga tgagttccgc aagcggatcg gcgtgctgga caccgagtac    540
accagaacag ataacctgaa gatgagagtg atcgagctgg ccctgaagca gatcaatgag    600
cacaccgata tcacagcctc ttatgagcag acaagaagg gccgcgtgat caccggcttc    660
agctttaagt tcaagcacaa gaagcagaac tctgacaaga caccaaagaa tagcgattcc    720
tctccccgga tcgtgaagca cagccagatc cctaccaaca tcgtgaagca gccagagaat    780
gccaagatgt ccgacctgga gcacagggca tctagggtga caggcgagat catgagaaat    840
aggctgagcg atcggttcaa gcagggcgac gagtccgcca tcgatatgat gaagagaatc    900
cagtccgaga tcatcaccga cgccatcgcc gatcagtggg aatctaaact ggaagagttt    960
ggagtcgtgt ttggagcaca tcaccatcat catcactga                          999
```

<210> SEQ ID NO 11
<211> LENGTH: 324
<212> TYPE: PRT
<213> ORGANISM: artificial sequence
<220> FEATURE:
<223> OTHER INFORMATION: MSBI1 Rep 27/154E mutant

<400> SEQUENCE: 11

```
Met Ser Asp Leu Ile Val Lys Asp Asn Ala Leu Met Asn Ala Ser Tyr
1               5                   10                  15

Asn Leu Ala Leu Val Glu Gln Arg Leu Ile Glu Leu Ala Ile Ile Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
            100                 105                 110

Ile Phe Ala Pro Ala Val Val Pro Leu Ile Thr Arg Leu Glu Glu Gln
        115                 120                 125

Phe Thr Gln Tyr Asp Ile Glu Gln Ile Ser Gly Leu Ser Ser Ala Tyr
    130                 135                 140

Ala Val Arg Met Tyr Glu Leu Leu Ile Glu Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Arg Val Ile Glu
            180                 185                 190

Leu Ala Leu Lys Gln Ile Asn Glu His Thr Asp Ile Thr Ala Ser Tyr
        195                 200                 205
```

```
Glu Gln His Lys Lys Gly Arg Val Ile Thr Gly Phe Ser Phe Lys Phe
    210                 215                 220

Lys His Lys Lys Gln Asn Ser Asp Lys Thr Pro Lys Asn Ser Asp Ser
225                 230                 235                 240

Ser Pro Arg Ile Val Lys His Ser Gln Ile Pro Thr Asn Ile Val Lys
                245                 250                 255

Gln Pro Glu Asn Ala Lys Met Ser Asp Leu Glu His Arg Ala Ser Arg
            260                 265                 270

Val Thr Gly Glu Ile Met Arg Asn Arg Leu Ser Asp Arg Phe Lys Gln
        275                 280                 285

Gly Asp Glu Ser Ala Ile Asp Met Met Lys Arg Ile Gln Ser Glu Ile
290                 295                 300

Ile Thr Asp Ala Ile Ala Asp Gln Trp Glu Ser Lys Leu Glu Glu Phe
305                 310                 315                 320

Gly Val Val Phe

<210> SEQ ID NO 12
<211> LENGTH: 319
<212> TYPE: PRT
<213> ORGANISM: artificial sequence
<220> FEATURE:
<223> OTHER INFORMATION: MSBI2 Rep 27/154E mutant

<400> SEQUENCE: 12

Met Ser Lys Leu Val Val Lys Asp Asn Ala Leu Met Asn Ala Ser Tyr
1               5                   10                  15

Asn Leu Asp Leu Val Glu Gln Arg Leu Ile Glu Leu Ala Ile Ile Glu
            20                  25                  30

Ala Arg Glu Ser Gly Lys Gly Ile Asn Ala Asn Asp Pro Leu Thr Val
        35                  40                  45

His Ala Glu Ser Tyr Ile Asn Gln Phe Gly Val His Arg Val Thr Ala
    50                  55                  60

Tyr Gln Ala Leu Lys Asp Ala Cys Asp Asn Leu Phe Ala Arg Gln Phe
65                  70                  75                  80

Ser Tyr Gln Ser Lys Ser Glu Lys Gly Asn Ile Gln Asn His Arg Ser
                85                  90                  95

Arg Trp Val Ser Glu Ile Ile Tyr Ile Asp Thr Glu Ala Thr Val Lys
            100                 105                 110

Ile Ile Phe Ala Pro Ala Ile Val Pro Leu Ile Thr Arg Leu Glu Glu
        115                 120                 125

Gln Phe Thr Lys Tyr Asp Ile Glu Gln Ile Ser Asp Leu Ser Ser Ala
130                 135                 140

Tyr Ala Ile Arg Leu Tyr Glu Leu Leu Ile Glu Trp Arg Ser Thr Gly
145                 150                 155                 160

Lys Thr Pro Ile Ile Gly Leu Gly Glu Phe Arg Asn Arg Val Gly Val
                165                 170                 175

Leu Asp Ser Glu Tyr His Arg Ile Ala His Leu Lys Glu Arg Val Ile
            180                 185                 190

Glu His Ser Ile Lys Gln Ile Asn Glu His Thr Asp Ile Thr Ala Thr
        195                 200                 205

Tyr Glu Gln His Lys Lys Gly Arg Thr Ile Thr Gly Phe Ser Phe Lys
    210                 215                 220

Phe Lys Gln Lys Lys Pro Lys Gln Ala Glu Ile Ala Thr Glu Thr Pro
225                 230                 235                 240
```

```
Lys Thr Ala Thr Asn Asp Pro Asp Thr Thr Lys Pro Leu Thr Glu Pro
                245                 250                 255

Gln Ile Ala Lys Tyr Ser Met Ile Leu Cys Lys Leu Gly Ser Ile Ser
            260                 265                 270

Asp Leu Ser Asn Phe Pro Asp Tyr Pro Ala Phe Ala Asn Trp Ile Gly
        275                 280                 285

Asn Ile Leu Arg Asn Pro Glu Lys Ala Asp Glu Gln Ile Ala Lys Arg
    290                 295                 300

Ile Phe Thr Ala Leu Lys Thr Glu Thr Asp Tyr Ser Lys Lys Asn
305                 310                 315
```

REP PROTEIN FOR USE IN A DIAGNOSTIC ASSAY

This application is a continuation of PCT/EP2018/068118, filed Jul. 4, 2018; which claims priority to EP Application No. 17180235.8, filed Jul. 7, 2017. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Dec. 27, 2019, and a size of 13.9 kilobytes. The Sequence Listing filed via EFS-Web is part of the specification and is hereby incorporated in its entirety by reference herein.

FIELD OF THE INVENTION

The invention relates to the detection and quantification of a DNA-replication-associated (Rep) protein for use in the diagnosis of a neurodegenerative disease such as, for example, multiple sclerosis (MS). In particular, the invention relates to a mutant MSBI1 genome-encoded Rep protein.

BACKGROUND OF THE INVENTION

The ethiology of multiple sclerosis (MS) has not been resolved. Thus, there is a demand for a biomarker for MS which could be used for diagnosing MS and/or monitoring MS or a treatment of MS and/or assessing a predisposition for MS.

Multiple sclerosis (MS) is characterized by demyelinization of MS lesions damaging nerve cells in the brain and spinal cord. MS symptoms either occur as episodes of sudden worsening (relapses, exacerbations, bouts, attacks) or as a gradual worsening over time (progressive forms). Demyelinization starts inflammatory processes which trigger T cells and the release of cytokines and antibodies. For the diagnosis of MS, among others, neuroimaging, analysis of the cerebrospinal fluid and evoked potentials are used.

A spectrum of 17 different, but partially related DNA molecules were isolated from different test material (multiple sclerosis (MS) brain tissue, bovine sera, milk) (Funk, Gunst et al. 2014, Gunst, Zur Hausen et al. 2014, Lamberto, Gunst et al. 2014, Whitley, Gunst et al. 2014).

Among these isolates two DNA molecules closely related to transmissible spongiform encephalophaty (TSE)-associated isolate Sphinx 1.76 (1,758 bp; accession no. HQ444404, (Manuelidis L. 2011)) were isolated from brain tissue from MS patients. These isolates were MSBI1.176 (MSBI, multiple sclerosis brain isolate) (1,766 bp) and MSBI2.176 (1,766 bp) which are designated as "MSBI1 genome" and "MSBI2 genome", respectively. MSBI1,176 shares 98% nucleotide similarity to the sequence of Sphinx 1.76. The large open reading frames (ORFs) of the isolates encode a putative DNA replication protein sharing high similarity between them. Another common feature is the presence of iteron-like tandem repeats. The alignment of this repeat region indicates a variation in the core of single nucleotides. This iteron-like repeats may constitute the binding sites for Rep proteins. The sequences of the isolates have been deposited in the EMBL Databank under accession numbers LK931491 (MSBI1.176) and LK931492 (MSBI2.176) (Whitley C. et al. 2014) and have been aligned and described in WO 2016/005064.

SUMMARY OF THE INVENTION

The present inventors have recently found that wild-type MSBI1 genome shows a significant production of transcribed RNA and MSBI1 genome-encoded Rep protein is expressed in human cells. They have found that the wild-type MSBI1 and MSBI2 genome-encoded Rep protein (MSBI1 Rep and MSBI2 Rep) represent a biomarker for pathogenicity screening assays. As DNA-replication-associated protein (RepB) the Rep protein has DNA binding activity and can be essential for initiation of replication of episomal or viral DNA molecules. However, Rep proteins which are structurally similar to the wild-type MSBI1 and 2 genome-encoded Rep show a marked potential of self-oligomerization and aggregation.

For diagnostic screening assays wild-type Rep protein antigens MSBI1 Rep and MSBI2 Rep were purified and stored under denaturing as well as reducing conditions to minimize aggregation or degradation effects on the protein. Unfortunately, the inventors observed that prior purifications of wild-type MSBI1 Rep protein under non-denaturing conditions indeed showed massive and visible protein aggregation which most obviously rendered the Rep protein inaccessible for affinity purification. Residual very small amounts of purified Rep protein aggregated within very short time scales (several hours) rendering the protein inadequate for further diagnostic assays. This in line with previous studies describing aggregation of Rep proteins comparable to MSBI1 Rep (Giraldo 2007, Torreira, Moreno-Del Alamo et al. 2015).

For diagnostic screening assays the stability and integrity of the protein antigen, which is used for detection of antigen-binding antibodies in blood samples, is of highest importance for reproducibility and reliability of such sensitive experiments. In this respect, both the shelf-life of the protein antigen during long term storage but also biophysical behaviour during the diagnostic screening assays itself (steps of coating, blocking, washing, detection antibody incubation) are pivotal for successful assays. In view of the observed aggregation behaviour of the wild-Type Rep proteins (MSBI1 Rep and MSBI2 Rep), however, there is a need for an improved Rep protein that does not have the aggregation and self-oligomerization properties as the wild-type Reps.

The inventors found out that the above negative properties can be avoided by a mutant protein. The present invention provides mutant MSBI1 Rep and MSBI2 Rep proteins which have at least two point mutations compared to the respective wild-type proteins and represent a biomarker for pathogenicity screening assays. The synthesized MSBI1 and MSBI2 Rep proteins are mutants derived from the wild type (wt) MSBI1 and MSBI2 genome-encoded Rep proteins as shown in SEQ ID. NO: 1 (MSBI1.176) and SEQ ID NO: 8 (MSBI 2.176). The synthesized mutant MSBI1 and MSBI2 Rep proteins provide a higher stability of the REP protein and less aggregation under in vitro conditions also in urea storage buffer. The synthesized mutant MSBI1 and MSBI2 Rep proteins are a more stable antigen as the wild type MSBI1 and MSBI2 Rep proteins for use in diagnostic screening assays.

Anti-Rep antibodies are used as pathogenic markers due to the link of pathogenic activity of the isolated DNA (e.g. MSBI1) agent with the Rep protein expression. Patient sera containing increased amounts of anti-Rep antibodies indicate that the corresponding patient was definitely exposed to Rep-related proteins or himself expressed Rep during a time period long enough to initiate a Rep specific immune response. As target for the human antibodies Rep protein is used as the antigen. Based on the quantification of the amount of anti Rep antibodies acute MS as well as a predisposition for MS can be diagnosed or monitored. Because it has been recognized that increased amount of induced anti-Rep antibodies or expressed Rep protein in a sample indicates the onset and/or status of MS, the increased amount of anti-Rep antibodies and Rep protein, respectively, can be used as pathogenic biomarker for the diagnosis of MS.

Advantageously, the pathogenic biomarker for MS can be detected in blood samples, such as serum or plasma samples, and it is not necessary to obtain samples from the cerebrospinal fluid.

Hence, the invention provides a DNA-replication-associated (Rep) protein which comprises (i) an amino acid sequence as depicted in SEQ ID NO:11;

(ii) a fragment of SEQ ID NO: 11 which is capable of binding an anti-Rep antibody specific for a protein comprising an amino acid sequences as depicted in SEQ ID NO: 11; or (iii) an amino acid sequence having a 90% or more homology to the amino acid sequence of (i) or (ii) and is capable of binding an anti-Rep antibody specific for a protein comprising an amino acid sequences as depicted in SEQ ID NO: 11.

In addition, the invention provides a DNA-replication-associated (Rep) protein which comprises (i) an amino acid sequence as depicted in SEQ ID NO:12;

(ii) a fragment of SEQ ID NO: 12 which is capable of binding an anti-Rep antibody specific for a protein comprising an amino acid sequences as depicted in SEQ ID NO: 12; or (iii) an amino acid sequence having a 90% or more homology to the amino acid sequence of (i) or (ii) and is capable of binding an anti-Rep antibody specific for a protein comprising an amino acid sequences as depicted in SEQ ID NO: 12.

The Rep protein of the present invention may be employed in virtually any assay format that employs a known antigen to detect antibodies or cell-mediated immune responses. Thus, the present invention also encompasses the detection of cell-mediated, e.g. T-cell immune responses against Rep protein.

In certain embodiments the invention provides a method of diagnosing a neurodegenerative disease in a subject comprising the steps of (a) incubating a sample from a subject with a Rep protein as defined above;

(b) detecting the amount of antibodies in the sample from the subject forming an immunological complex with Rep protein; and (c) correlating the amount of antibody bound to Rep protein, as compared to an amount in a control sample, with a diagnosis of a neurodegenerative disease.

In particular embodiments the invention provides a method of diagnosing MS in a subject comprising the steps of (a) incubating a sample from a subject with a Rep protein;

(b) detecting the amount of antibodies in the sample from the subject forming an immunological complex with Rep protein; and (c) correlating the amount of antibody bound to Rep protein, as compared to an amount in a control sample, with a diagnosis of MS.

An increased amount of anti-Rep antibodies in a sample from a subject as compared to anti-Rep antibody amount in a control sample correlates with a diagnosis of a neurodegenerative disease, e.g. MS, i.e. is indicative for MS. In certain embodiments diagnosis of a neurodegenerative disease, e.g. MS or a predisposition for a neurodegenerative disease, e.g. MS, is indicated by an increased amount of anti-Rep antibodies of at least 2 fold as compared to a control sample.

In particular embodiments the Rep protein is immobilized, e.g. attached to a support or carrier, followed by incubating the immobilized Rep protein with the sample from the subject.

In other embodiments the Rep protein is expressed in cells followed by incubating the cells with the sample from the subject.

In certain embodiments the amount of antibodies forming an immunological complex with Rep protein is quantified by an additional binding agent coupled to a signal generating compound which is capable of binding to the anti-Rep antibodies of the immunological complex, for example a detectably labeled secondary antibody, preferably anti-human antibody.

In other embodiments the antibodies in the sample from the subject are immobilized followed by incubating with a defined amount of Rep protein.

Preferably, the sample from the subject and the control sample is a blood sample such as a serum or a plasma sample.

In addition, the inventors have generated anti-Rep antibody that bind to an epitope that is within an amino acid sequence selected from the group consisting of amino acids from 1 to 136, from 137 to 229 and from 230 to 324 of SEQ ID NO:1 or 11. For example, the antibody binds to an epitope comprised by SEQ ID NO:2 or SEQ ID NO:3.

In further embodiments the invention provides a kit for use in the diagnosis of MS comprising (a) Rep protein MSBI1 Rep 27/154E or MSBI2 Rep 27/154E, (b) an additional binding agent coupled to a signal generating compound, for example, an anti-human antibody coupled to a detectable label and capable of binding to anti-Rep antibody according to the invention, and (c) a solid matrix suitable for immobilizing a Rep protein according to (a) or anti-Rep antibodies, wherein aid antibodies are suspected in a sample, in particular a serum or a plasma sample.

In particular embodiments the kit is put together for use in an immunoassay, for example selected from the group consisting of enzyme-linked immunosorbent assay (ELISA), radioimmunoassay (RIA), enzyme immune assay (EIA), fluorescence immunoassay (FIA), luminescence immunoassay (LIA) and strip assay.

DETAIL DESCRIPTION OF THE INVENTION

Figure 1:
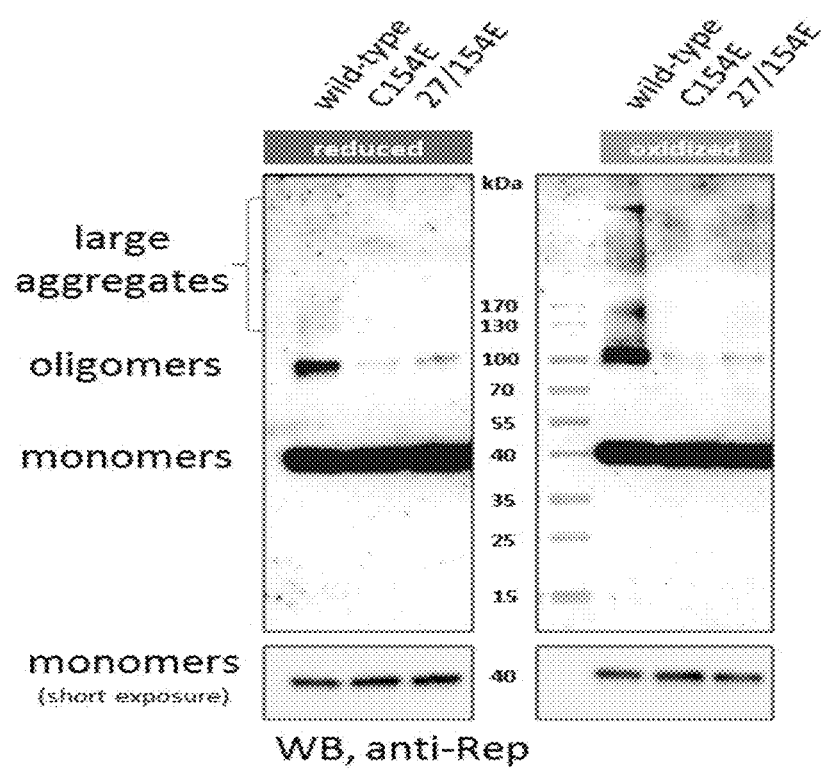
FIG. 1 Rep protein was overexpressed by transient transfection of HEK293TT with a pcDNA3.1(−) plasmid coding for either MSBI1 Rep wild type (WT) or mutant MSBI1 Rep 27/154E for 72 hours. Cells were trypsinized, washed in PBS and sonified in lysis buffer (50 mM Tris pH 7.6, 150 mM NaCl, 1.5% Triton X-100, 5 mM imidazole, 5 mM betamercaptoethanol, 1× proteinase inhibitor mix). After incubation (30 min, 4° C.) and centrifugation (30 min, 10,000 g, 4° C.) non-denaturing protein purification was carried out by binding to protein to 1 ml equilibrated Ni-NTA beads (Clontech), washing with 10 column volumes washing buffer (lysis buffer containing 55 mM imidazole) and elution (lysis buffer containing 300 mM imidazole). After protein quantification by NanoDrop and Bradford, equal amounts of protein (500 ng per lane) were boiled in Lammli buffer with (reduced) or without (oxidized) 5 mM beta mercaptoethanol and analyzed by SDS-PAGE and western blotting with anti-Rep antibodies.

The invention provides mutant Rep proteins and diagnostic screening assays for the presence of anti-Rep antibodies as pathogenic markers. Samples containing increased amounts of anti-Rep antibodies indicate that the corresponding subject was definitely exposed to Rep-related protein or himself expressed Rep protein during a time period long enough to induce a Rep protein specific immune response. With such screening assays a diagnosis, prognosis and monitoring of MS based on the quantification of anti-Rep antibodies can be conducted.

"Rep protein" as used herein refers to a DNA-replication-associated protein (RepB). The Rep protein comprises DNA binding activity and could be essential for initiation of replication of episomal/viral DNA molecules. In general Rep protein refers to a Rep protein from the group of the Small Sphinx Genome (Whitley et al., 2014). In particular, the Rep protein is a synthesized genome-encoded Rep protein MSBI1 Rep 27/154E and a MSBI2 genome-encoded Rep 27/154E protein. Preferably, the synthesized MSBI1 Rep protein has the amino acid sequence as depicted in SEQ ID NO:11 and is derived from MSBI1.176 deposited in the EMBL databank under the acc. no. LK931491 which has the amino acid sequence as depicted in SEQ ID NO:1, or the synthesized Rep protein has the amino acid sequence as depicted in SEQ ID NO:12 and is derived from MSBI2.176 deposited in the EMBL databank under the acc. no. LK931492 which has the amino acid sequence as depicted in SEQ ID NO:8.

In a particular preferred embodiment the Rep protein comprises a N-terminal region conserved among small Sphinx genomes consisting essentially of amino acids from 1 to 229 of SEQ ID NO: 11 or 12 and a C-terminal variable region specific for MSBI1.176 consisting essentially from amino acids 230 to 324 of SEQ ID NO: 11, or C-terminal variable region specific for MSBI2.176 consisting essentially from amino acids 230 to 324 of SEQ ID NO: 12. The N-terminal conserved region comprises a putative, first DNA binding domain consisting essentially of amino acids from 1 to 136 of SEQ ID NOs: 1, 8, 11 and 12 and a second putative DNA binding domain consisting essentially of amino acids from 137 to 229 of SEQ ID NOs:1, 8, 11 and 12.

"Rep protein" also encompasses fragments and variants of the protein which are capable of binding an anti-Rep antibody specific for Rep protein having the amino acid sequence of SEQ ID NO: 11 or 12. Preferably, such a fragment is an immunogenic fragment of the protein having the amino acid sequence of SEQ ID NO: 11 or 12 which encompasses at least one epitope for an anti-Rep protein antibody against the Rep protein of SEQ ID NO:11 or SEQ ID NO:12 and, preferably, comprises at least 7, 8, 9, 10, 15, 20, 25 or 50 contiguous amino acids. In particular embodiments the fragment comprises or consists essentially of a domain of the Rep protein, for example, the N-terminal conserved region, the C-terminal variable region, the first or second DNA binding domain. A variant of the protein with SEQ ID NO:11 or SEQ ID NO:12 comprises one or more amino acid deletions, substitutions or additions compared to SEQ ID NO:11 or SEQ ID No. 12 and has a homology of at least 90%, 91%, 92%, 93%, 94%, 95%, 96%, 97%, 98% or 99% to the amino acid sequence of SEQ ID NO:11 or SEQ ID NO: 12, wherein the variant is capable of binding an anti-Rep antibody specific for a Rep protein having the amino acid sequence of SEQ ID NO:11 or SEQ ID NO:12. Included within the definition of variant are, for example, polypeptides containing one or more analogues of an amino acid (including, for example, unnatural amino acids, peptide nucleic acid (PNA), etc.), polypeptides with substituted linkages, as well as other modifications known in the art, both naturally occurring and non-naturally occurring. The term Rep protein includes fusion proteins with a heterologous amino acid sequence, with a leader sequence or with a Tag-sequence and the like. For example the Rep protein may be fused to a Tag-sequence, for example, selected from the group consisting of His$_6$-Tag (SEQ ID NO:4), T7-Tag (SEQ ID NO:5), FLAG-Tag (SEQ ID NO:6) and Strep-II-Tag (SEQ ID NO:7).

The synthesized MSBI1 Rep protein (MSBI1 Rep 27/154E) or MSBI2 Rep protein (MSBI2 Rep 27/154E) of the invention, including the Rep fragments and Rep variants as defined above, can be prepared by classical chemical synthesis. The synthesis can be carried out in homogeneous solution or in solid phase. The polypeptides according to this invention can also be prepared by means of recombinant DNA techniques. For example, MSBI1 Rep 27/154E was engineered in which the aggregation potential of two amino acid sequences between residues 25-31 (LLILLAII) and residues 151-155 (LLICW) was minimized by two single point mutations. The basis for the cloning was a MSBI1 Rep DNA sequence which was codon-optimized for Rep expression in the human system encoding the original MSBI1 Rep primary amino acid sequence. The nucleotides coding for amino acid 27 (L, Leucine, DNA codon CTA) as well as the nucleotides coding for amino acid 154 (C, Cysteine, DNA codon TGT) were substituted by nucleotides coding for the amino acid glutamic acid (E, DNA codon GAG) equaling the final DNA sequence SEQ ID NO: 11. The net aggregation potential of this Rep double mutant was minimized to a score of 141 being in the range of non-aggregation prone proteins.

Figure 4:
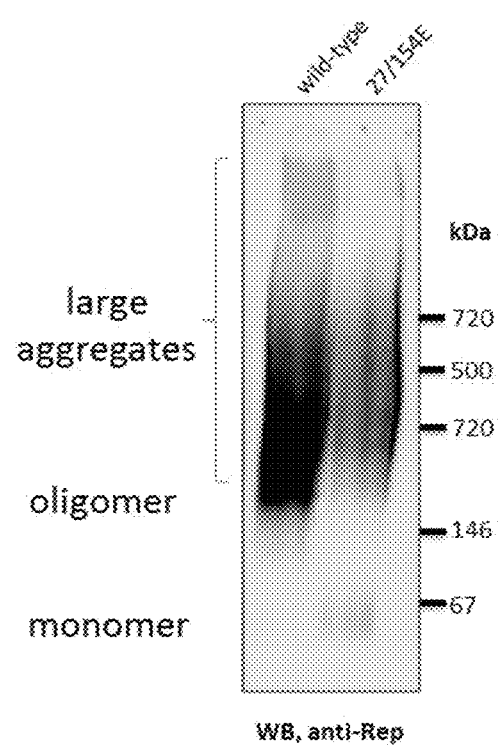
FIG. 4 Rep protein was purified from E. coli under denaturing conditions (protocol see below). 5 µg MSBI1 Rep wt or mutant MSBI1 Rep 27/154E were used for BN-PAGE and anti-Rep immunodetection.

As shown in the Examples (FIG. 2, 3), the Rep 27/154E mutant showed a significant reduction (>50%) of Rep oligomers and larger aggregates when compared with the wild-type Rep protein. Western blotting also showed significantly less Rep oligomers as well as less high molecular weight aggregates (FIG. 4). An additional species of most obviously monomeric Rep protein was detected under native PAGE conditions only for the Rep mutant. Clearly, the intensity of high molecular weight aggregates is significantly reduced for the 27/154E Rep double mutant. In general, the presence of Rep aggregates is higher for proteins which were purified under non-denaturing conditions. Anyways, also proteins purified and stored under denaturing conditions show very strong aggregation, which is significantly reduced for the Rep double mutant. This is of special interest, as ELISA experimental setups rely and renaturation of the surface-bound protein antigens, because antibody antigen binding necessitates native conditions.

The wild type Rep proteins can be prepared by classical chemical synthesis. The synthesis can be carried out in homogeneous solution or in solid phase. The polypeptides according to this invention can also be prepared by means of recombinant DNA techniques. An example for producing and purification of a wild type Rep protein is shown in Example 1.

"Subject" as used herein refers to a mammalian individual or patient, including murines, cattle, for example bovines, simians and humans. Preferably, subject is a human patient.

"Sample" as used herein refers to a biological sample encompassing liquid and solid samples. Liquid samples encompass blood liquids such as, for example, sera or plasma and cerebrospinal fluid (CSF). Solid samples encompass tissue samples such as tissue cultures or biopsy specimen.

"Correlates with" as used herein refers to an amount, i.e. level or titer, of anti-Rep antibodies and Rep protein, respectively, with a significant correlation with a disease status of, for example, MS. The correlation is determined by detecting the extent of difference in the amount present in a sample from a subject to be tested and a control sample. "Control sample" means a single sample or an average of various, i.e. more than two, control samples. The control is taken from a healthy individual who has not been diagnosed for MS. Alternatively, the correlation may be theoretically determined by detecting the extent of difference in the amount present in a sample for a subject to be tested with a predetermined cut-off value. A cut-off value is a reference value with statistically significant separation between different disease status, e.g. between healthy and diseased status. The cut-off value can be determined by statistical analysis of a sufficiently large panel of test samples from patients with disease history and samples from healthy test group by statistical tests known in the art.

In certain embodiments a diagnosis, for example of MS, is indicated by an at least 2 fold, 3 fold, 4 fold, 5 fold, 10 fold, 50 fold, 100 fold, 500 fold or 1000 fold increased amount of protein, i.e Rep protein and anti-Rep-antibodies, respectively, in the sample from the subject as compared to a control sample.

"Anti-Rep antibody" as used herein refers to an antibody binding at a detectable level to Rep protein in the methods of the invention which affinity is more strongly to the Rep protein of the invention than to a non-Rep protein. Preferably, the antigen affinity for Rep protein is at least 2 fold larger than background binding. In particular the anti-Rep antibody is specific for the MSBI1 Rep having the amino acid sequence of SEQ ID NO:1 or 11 or MSBI2 Rep having the amino acid sequence of SEQ ID No: 8 or 12. In particular embodiments the antibody is cross-specific for MSBI1 Rep or MSBI2 Rep.

A common feature of all assays is that the Rep protein is contacted with a sample suspected of containing anti-Rep protein antibodies under conditions that permit the Rep protein to bind to any such antibody present in the sample. Such conditions will typically be physiologic temperature, pH and ionic strength using an excess of Rep protein. The incubation of the Rep protein with the sample is followed by detection of immune complexes comprised of the antigen. In certain embodiments either the Rep protein is coupled to a signal generating compound, e.g. detectable label, or an additional binding agent, e.g. secondary anti-human antibody, coupled to a signal generating compound is used for detecting the immune complex.

Anti-Rep antibodies can be detected and quantified in assays based on Rep protein as protein antigen, which serves as target for the mammalian, e.g. human, antibodies suspected in the sample. Preferably, the Rep protein is purified (e.g. see Example 1) and the samples can be, for example, serum or plasma samples. The methods include immobilization of Rep protein on a matrix followed by incubation of the immobilized Rep protein with the samples. Finally, the Rep-bound antibodies of the formed immunological complex between Rep protein and antibodies of the samples are quantified by a detection binding agent coupled to a signal generating compound, e.g. secondary HRP-(horseradish-peroxidase)-coupled detection antibody allowing for HRP-substrate based quantification. This signal generating compound or label is in itself detectable or may be reacted with an additional compound to generate a detectable product.

In other embodiments anti-Rep antibodies are indirectly quantified in that first the antibodies of the sample are immobilized on a matrix, followed by incubation with a defined amount of Rep protein, wherein the anti-Rep antibodies immobilized and present on the matrix capture the Rep protein from the protein-sample liquid mixture, followed by quantification of the bound Rep protein.

In other embodiments Rep protein can be expressed in cells and these cells are incubated with the sample. Thereafter, anti-Rep antibodies from the sample bound to the Rep protein expressed by cells are detected and quantified.

Design of the immunoassay is subject to a great deal of variation, and many formats are known in the art. Protocols may, for example, use solid supports, or immunoprecipitation. Most assays involve the use of binding agents coupled to signal generating compounds, for example labelled antibody or labelled Rep protein; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be in a heterogeneous or in a homogeneous format, and of a standard or competitive type. In a heterogeneous format, the polypeptide (Rep protein or anti-Rep antibody) is typically bound to a solid matrix or support or carrier to facilitate separation of the sample from the polypeptide after incubation. Examples of solid supports that can be used are nitrocellulose (e. g., in membrane or microtiter well form), polyvinyl chloride (e. g., in sheets or microtiter wells), polystyrene latex (e. g., in beads or microtiter plates, polyvinylidine fluoride (known as Immunolon), diazotized paper, nylon membranes, activated beads, and Protein A beads. The solid support containing the antigenic polypeptides is typically washed after separating it from the test sample, and prior to detection of bound anti-Rep antibodies. Both standard and competitive formats are known in the art.

In a homogeneous format, the test sample is incubated with the Rep protein in solution. For example, it may be under conditions that will precipitate any Rep protein-antibody complexes which are formed. Both standard and competitive formats for these assays are known in the art.

In a standard format, the amount of anti-Rep antibodies in the antibody-Rep protein complexes is directly monitored. This may be accomplished by determining whether (labelled) anti-xenogeneic (e. g. anti-human) antibodies which recognize an epitope on anti-Rep antibodies will bind due to complex formation. In a competitive format, the amount of anti-Rep antibodies in the sample is deduced by monitoring the competitive effect on the binding of a known amount of labelled antibody (or other competing ligand) in the complex.

Complexes formed comprising anti-Rep antibody (or in the case of competitive assays, the amount of competing antibody) are detected by any of a number of known techniques, depending on the format. For example, unlabeled anti-Rep antibodies in the complex may be detected using a conjugate of anti-xenogeneic Ig complexed with a label (e. g. an enzyme label, such as, for example, HRP).

In an immunoprecipitation or agglutination assay format the reaction between the Rep protein and the anti-Rep antibody forms a network that precipitates from the solution or suspension and forms a visible layer or film of precipitate. If no anti-Rep antibody is present in the sample, no visible precipitate is formed.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase (HRP) and beta-galactosidase. Examples of enhancer compounds include biotin, anti-biotin and avidin. Examples of enhancer compounds binding members include biotin, anti-biotin and avidin.

In further embodiments the invention provides methods wherein an increased amount of Rep protein in a sample correlates with a diagnosis or predisposition of a neurodegenerative disease, for example MS, or is used for monitoring the disease, for example MS, or monitoring the treatment of the disease, for example MS. In such embodiments the Rep protein in the sample is detected by anti-Rep antibodies.

Such methods comprise the steps of
(a) detecting the amount of Rep protein in a sample from a subject by anti-Rep antibodies; and
(b) correlating the amount of Rep protein detected in the sample from a subject in step (a) as compared to an amount in a control sample with a diagnosis of a neurodegenerative disease, for example MS.

Examples for assays which can be used in such methods for the detection of Rep protein in serum or plasma samples include, but are not limited to immunoprecipitation, immunofluorescence, dot blotting and Western Blot.

For example, a serum sample may be incubated with anti-Rep protein antibodies to capture the Rep protein in the sample, followed by a step of immunoprecipitation of Rep protein and, thereafter, a step of detection by SDS-PAGE and Western Blot.

In a further example, a dot blot membrane may be incubated with serum, followed by the step of a SDS-PAGE and Western Blot.

In a further example, serum dilutions of the sample are loaded on SDS-Page followed by a Western Blot.

In further embodiments Rep protein is detected in tissue samples by immunohistochemical methods or immunofluorescence microscopy.

In certain embodiments anti-Rep antibodies are used for the detection or capturing of the Rep protein in the sample.

The term "antibody", preferably, relates to antibodies which consist essentially of pooled polyclonal antibodies with different epitopic specificities, as well as distinct monoclonal antibody preparations. As used herein, the term "antibody" (Ab) or "monoclonal antibody" (Mab) is meant to include intact immunoglobulin molecules as well as antibody fragments (such as, for example, Fab and F(ab')2 fragments) which are capable of specifically binding to Rep protein. Fab and F(ab')2 fragments lack the Fc fragment of intact antibody, clear more rapidly from the circulation, and may have less non-specific tissue binding than an intact antibody. Thus, these fragments are preferred, as well as the products of a FAB or other immunoglobulin expression library. Moreover, antibodies useful for the purposes of the present invention include chimerical, single chain, multifunctional (e.g. bispecific) and humanized antibodies or human antibodies.

In certain embodiments the antibody or antigen binding fragment thereof is coupled to a signal generating compound, e.g., carries a detectable label. The antibody/fragment can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

Figure 6:
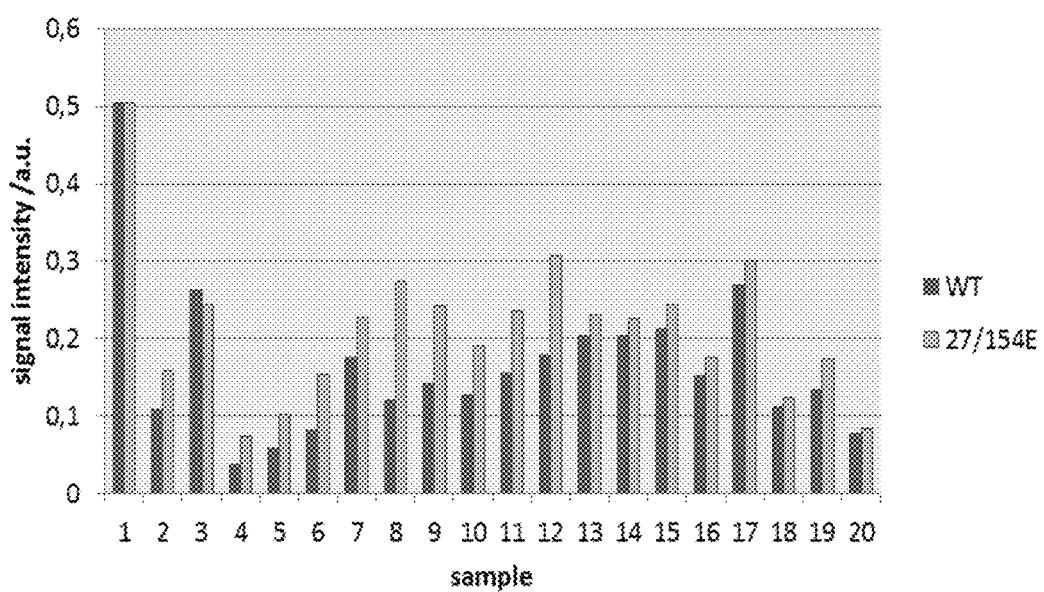
FIG. 6 ELISA plates (Maxisorp, Thermo Fisher Scientific) were coated either with purified denatured MSBI1 Rep wt or mutant MSBI1 Rep 27/154E at 4° C. overnight in 1:1 dilution of 1×PBS/8 M urea (200 ng protein per well). Blocking was performed in superblock assay buffer for 2 h at RT. Serum incubation (1:500 in superblock buffer) was performed for 1 h at 37° C. Rep-bound human IgG antibodies were quantified with an HRP-coupled goat anti-human secondary antibody (1:5000 dilution, 1 h at 37° C.) in duplicate analysis (washing with PBS 0.1% Tween, TMB ELISA substrate from Thermo Fisher Scientific, readout at 450 nm, signal normalized to BSA control).

As shown in the Example part, the newly engineered double Rep mutant shows a comparable ELISA coating performance when compared to the wild-type Rep protein. Additionally, the reactivity of Rep-reactive antibodies in human MS sera was increased by about 40% on average when using the 27/154E Rep double mutant as antigen when compared to wild-type Rep in ELISA assays (FIG. 6.)

The inventors have also raised (generated) anti-Rep antibodies against a Rep protein having the amino acid sequence of SEQ ID NO:1 or SEQ ID NO:8 or a fragment thereof by methods well known to those skilled in the art. These anti-Rep antibodies are used for binding to several or all kinds of Rep proteins from the group of the Small Sphinx Genome (anti-Small-Sphinx-like Rep antibody or anti-SSL- Rep antibody). Such anti-SSLRep antibody binds to an epitope within the conserved N-terminal region of the Rep protein from amino acids 1 to 229 of SEQ ID NO:1. Anti-Rep antibodies of the anti-SSLRep type are used which bind to an epitope within SEQ ID NO:2 (amino acids 32-49 of SEQ ID NO:1) or SEQ ID NO:3 (amino acids 197-216 of SEQ ID NO:1). The peptide fragments of SEQ ID NO:2 and SEQ ID NO:3 are highly conserved among the Rep proteins from the Small Sphinx Genome group and appear to be exposed due to their hydrophilic character. Anti-Rep antibodies of the anti-SSLRep type may be produced by immunization, for example of mice or guinea pig, by peptides consisting essentially of the amino acid sequences as depicted in SEQ ID NOs:2 or 3; or by other immunogenic fragments, preferably comprising at least 8-15 amino acids, derived from the conserved N-terminal Rep protein region from amino acids 1 to 229 of SEQ ID NO:1.

Such antibodies have been produced, for example, by immunization of a mammal such as mice or guinea pig with a full-length Rep protein having the amino acid sequence of SEQ ID NO:1.

These anti-Rep antibodies are capable of detecting Rep protein up to ranges from picogramm to femtogramm in different kinds of body liquids such as, for example, blood, serum, spinal fluid or cerebral fluid.

Either a specific kind of anti-Rep antibody or a pool of two or more different kinds of anti-Rep antibodies may be used. If a pool of different kinds of anti-Rep antibodies is used, the anti-Rep antibody pool may comprise different anti-Rep antibodies binding to different epitopes within different domains of the Rep protein, e.g. first DNA binding domain (e.g. aa 1-136 of SEQ ID NO:1), second DNA binding domain (e.g. aa 137-229 of SEQ ID NO:2) and/or variable domain (e.g. aa 230-324 of SEQ ID NO:1), in particular, of MSBI1 Rep protein (SEQ ID NO:1).

In view of the only two single point mutations in the two DNA binding domains and the maintenance of the same sequence in the variable domains, these antibodies also recognize the mutant proteins of SEQ ID Nos. 11 and 12.

For the detection of a Rep protein by anti-Rep antibodies methods such as, for example, Western Blot, immunofluorescence microscopy or immunohistochemical methods may be applied.

Anti-Rep antibodies are capable of detecting a Rep protein at certain cellular localizations. For instance the anti-Rep antibody may detect the Rep protein in cytoplasma, nuclear membrane and nucleus or detect speckles in cytoplasma. Examples of such group of anti-Rep antibodies are shown in Table 1:

| Antibody Group | RepProtein Localization | Specificity | Antibody | DSMZ deposit |
|---|---|---|---|---|
| Group A | cytoplasm + nuclear membrane (+nucleus) | MSBI1 + small-sphinx-like | ABO1 523-1-1 | DSM ACC3327 |
| Group B | speckles cytoplasm | in MSBI1 + small-sphinx-like | ABO2 304-4-1 | DSM ACC3328 |
| Group C | cytoplasm + nuclear membrane (+nucleus) | MSBI1 specific | MSBI1 381-6-2 | DSM ACC3329 |
| Group D | speckles in cytoplasm | MSBI1 specific | D1: MSBI1 961-2-2 D2: MSBI1 761-5-1 | DSM ACC3330 |

Anti-Rep antibodies of group A have an epitope within the amino acid sequence depicted in SEQ ID NO:3 (aa 198-217 of SEQ ID NO:1) and are capable of detecting MSBI1 Rep and Rep proteins comprising this conserved epitope of the Small Sphinx Genome group (e.g. MSBI2, CMI1, CMI4). In immunofluorescence assays such anti-Rep antibodies detect a specific Rep localization pattern, wherein the main localization is homogeneously distributed over the cytoplasm and nuclear membrane; and additional weak and homogeneously distributed localization is seen in the nucleus. An example of such a group A antibody is antibody AB01 523-1-1 (DSM ACC3327) which was employed in the examples as group A antibody.

Anti-Rep antibodies of group B have an epitope within the amino acid sequence depicted in SEQ ID NO:2 (aa 33-50 of SEQ ID NO:1) and are capable of detecting MSBI1 Rep and Rep proteins comprising this conserved epitope of the Small Sphinx Genome group (e.g. MSBI2, CMI1, CMI4). In immunofluorescence assays such anti-Rep antibodies detect specifically speckles (cytoplasmatic aggregations) of the Rep protein (often in the periphery of the nuclear membrane). An example of such a group B antibody is the antibody designated as AB02 304-4-1 (DSM ACC3328) which was employed in the examples as group B antibody.

Anti-Rep antibodies of group C detect specifically a structural epitope of MSBI1 (SEQ ID NO:1). In immunofluorescence assays such anti-Rep antibodies detect a specific Rep localization pattern, wherein the main localization is homogeneously distributed over the cytoplasm and nuclear membrane; and additional weak and homogeneously distributed localization is seen in the nucleus. An example of such a group C antibody is antibody MSBI1 381-6-2 (DSM ACC3329) which was employed in the examples as group C antibody.

Anti-Rep antibodies of group D detect specifically a structural epitope of MSBI1 (SEQ ID NO:1), where antibody MSBI1 961-2-2 designated as "D1" detects an epitope depicted in SEQ ID NO:9 (aa 281-287) in the C-terminal domain of MSBI1. Antibody MSBI1 761-5-1 (DSM ACC3328) designated as "D2" detects a 3D structural epitope of MSBI1 which is exclusively accessible under in vivo conditions and is not accessible in Western Blots. In immunofluorescence assays such anti-Rep antibodies detect specifically speckles (cytoplasmatic aggregations) of the Rep protein (often in the periphery of the nuclear membrane.

In certain embodiments the anti-Rep antibodies of groups A, B, C or D; or a combination of anti-Rep antibodies of at least two different groups A, B, C or D are used to determine the kind of Rep protein localization in a probe and if such a Rep protein localization correlates with a pathogen function. For instance, if speckles are present. In certain embodiments, i.e., methods or kits of the invention, at least one anti-Rep antibody selected from groups A and B is combined with at least one anti-Rep antibody selected from groups C and D. In particular embodiments, i.e., methods or kits of the invention, an anti-Rep antibody of group A is combined with at least one further anti-Rep antibody selected from the groups B, C, and D. For instance, an anti-Rep antibody of group A may be combined with further anti-Rep antibodies of groups C and D. Such combinations of anti-Rep antibodies of different groups increases the distinctness of the diagnostic assessment, in particular for the diagnosis of MS.

The following antibodies were deposited with the Deutsche Sammlung für Mikroorganismen and Zellkulturen (DSMZ) [German Collection of Microorganisms and Cell Cultures] on Sep. 28, 2017:
antibody AB01 523-1-1 under DSM ACC3327;
antibody AB02 304-4-1 under DSM ACC3328;
antibody MSBI1 381-6-2 under DSM ACC3329; and
antibody MSBI1 761-5-1 under DSM ACC3330.

Antibody MSBI1 961-2-2 has been deposited with DSMZ on Oct. 6, 2017.

In a preferred embodiment the anti-Rep antibodies of groups A, B, C or D; or a combination of anti-Rep antibodies of at least two different groups A, B, C or D are used to determine the synthesized MSBI1 Rep genome encoded Rep protein (MSBI1 Rep 27/154E or MSBI2 Rep 27/154E)).

In further embodiments a kit for use in the diagnosis of MS is provided. The kit may include material for detecting anti-Rep antibodies and/or Rep protein together with instructions for use of the materials in assays for the diagnosis of MS. The kit may comprise one or more of the following components: a biomarker according to the invention, i.e. Rep protein and anti-Rep antibodies, respectively; a signal generating compound, a solid matrix for attaching a capturing agent, a diluent for the samples, a wash buffer. Signal generating compound refers to a detectable label which is either coupled to an additional binding agent capable of binding to the biomarker of the invention or directly coupled with the biomarker of the invention.

The invention is further illustrated by, but not limited to, the following examples:

EXAMPLES

Example 1

MSBI1 Rep Protein Purification

A nucleotide acid molecule encoding full-length Rep open reading frame (ORF) identified within the MSBI1 genome is cloned into an expression plasmid (pEXP5-CT, Invitrogen) enabling protein expression based on an *E. coli* high yield cell free in vitro translation system (Expressway™ Cell-Free *E. coli* Expression System, Invitrogen). The synthesized Rep protein having the amino acid sequence of SEQ ID NO:1 within the in vitro translation reaction is denaturated by adding 20 reaction volumes 8 M urea sample buffer pH 8.0 containing 100 mM NaH2PO4, 10 mM Tris HCl, pH 8.0, 5 mM imidazole. The Rep protein is subsequently purified under denaturating conditions (20 mM imidazole for washing and 300 mM imidazole for protein elution) based on a C-terminal His6-tag fused to the Rep protein. Quality of purification is determined by Coomassie protein staining and Western Blotting with anti-Rep protein antibodies. The Rep protein purity is densitometrically calculated and greater 95%. The purified protein is either directly used for ELISA-based serum screening or subjected to SDS-Page followed by transfer blotting onto nitrocellulose membranes for serum incubation of 1D-size-resolved Rep protein membrane stripes.

Example 2

A. Characterization of Wildtype or Mutant Rep Protein Under Denaturing Conditions Using SDS-PAGE and Western Blotting The properties of the purified Rep antigens (wildtype and mutant Rep) were characterized by different sets of experiments. Rep protein, which was purified under non-denaturing (native) conditions from human HEK293TT cell line, showed significantly less levels of Rep oligomers (100 kDa band) and less heavy molecular weight aggregates for the single C154E and double 27/154E mutants when compared with the wildtype both under reducing and oxidizing sample loading conditions when subjected to SDS-PAGE and anti-Rep western blotting (FIG. 1).

Figure 2:
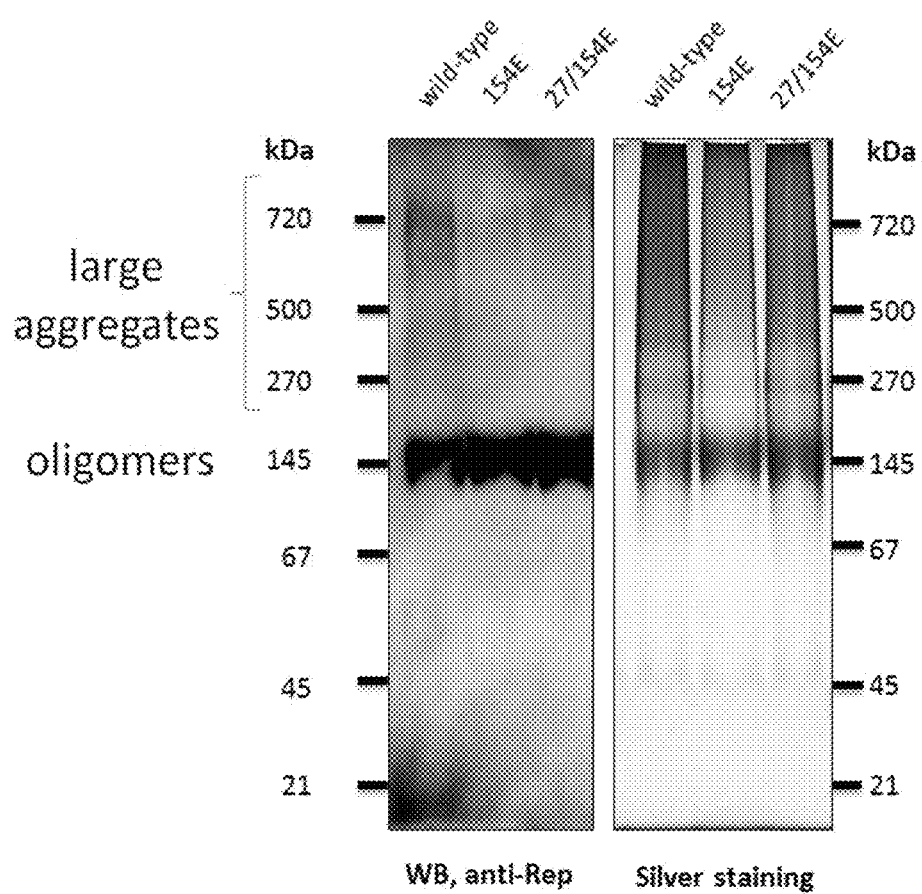
FIG. 2 Rep protein was purified under non-denaturing conditions as above. 2000 ng Rep protein were subjected to BN-PAGE (Serva) and stained either by anti-Rep immunodetection or protein silver staining.

B. Characterization of Wildtype or Mutant Rep Protein Under Non-Denaturing Conditions Using Native PAGE Characterization of the same non-denatured (native) Rep proteins by blue native PAGE also showed significantly less high molecular weight protein aggregates (high molecular weight smear) for the double mutant when compared to the wildtype, both for detection by western blotting (WB, anti-Rep) or by high sensitivity total protein staining (silver staining) (FIG. 2). However, in general, under native PAGE conditions the oligomeric species of Rep (MW of about 150 kDa) represents the dominating Rep protein species. These might be either trimers or tetramers of monomeric Rep (38.2 kDa theoretical MW).

Figure 3:
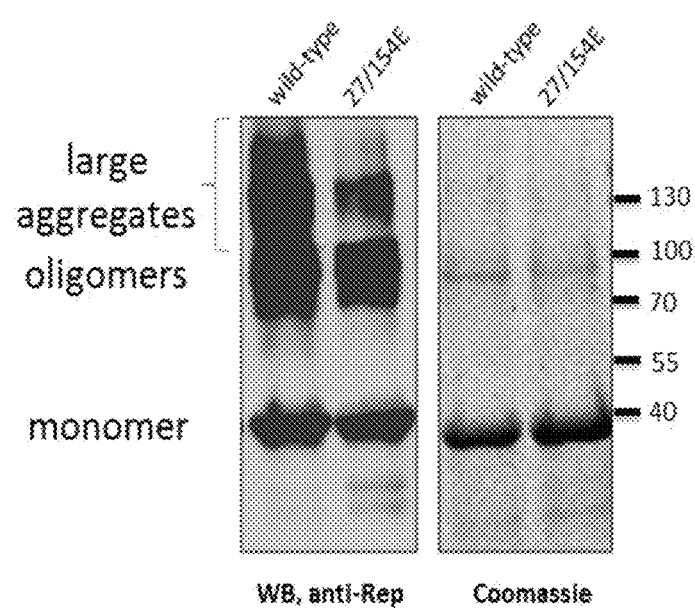
FIG. 3 Rep protein was purified from E. coli under denaturing conditions (protocol see below). Either 2 µg (western blot) or 5 µg (Coomassie staining) of purified MSBI1 Rep wt or mutant MSBI1 Rep 27/154E were characterized by anti-Rep immunodetection or Coomassie protein staining following SDS-PAGE.

C. Characterization of Wildtype or Mutant Rep Protein Under Denaturing Conditions Using SDS-PA and Western Blotting For standard ELISA assays, the Rep protein was purified under denaturing conditions from *E. coli* for high yield production and better protein stability (see protocol below). To characterize aggregation of denatured Rep WT and Rep MUT, the proteins were buffered for 1 h in PBS, to mimic renaturing ELISA coating and blocking conditions, and then subjected to either SDS-PAGE and western blotting with anti-Rep antibodies or Coomassie protein staining (FIG. 3). Again, the Rep mutant showed a significant reduction (>50%) of Rep oligomers and larger aggregates when compared with the wild-type Rep protein.

D. Characterization of Wildtype or Mutant Rep Protein Under denaturing conditions using BN-PAGE and Western Blotting Characterization of the same samples (each 5 µg) on BN-PAGE and subsequent anti-Rep western blotting also showed significantly less Rep oligomers as well as less high molecular weight aggregates (FIG. 4). An additional species of most obviously monomeric Rep protein was detected under native PAGE conditions only for the Rep mutant.

All results show existence of highly stable Rep oligomers (MW 110 kDa), which even resist SDS treatment during SDS-PAGE. Also highly stable Rep aggregates covering even higher molecular weight ranges (120-170 kDa and higher) are detectable by SDS-PAGE and western blotting. Clearly, the intensity of such high molecular weight aggregates is significantly reduced for the 27/154E Rep double mutant. In general, the presence of Rep aggregates is higher for proteins which were purified under non-denaturing conditions. Anyways, also proteins purified and stored under denaturing conditions show very strong aggregation, which is significantly reduced for the Rep double mutant. This is of special interest, as ELISA experimental setups rely and renaturation of the surface-bound protein antigens, because antibody antigen binding necessitates native conditions.

Example 3

A. ELISA Coating Performance of Wildtype or Mutant Rep Protein

Figure 5:
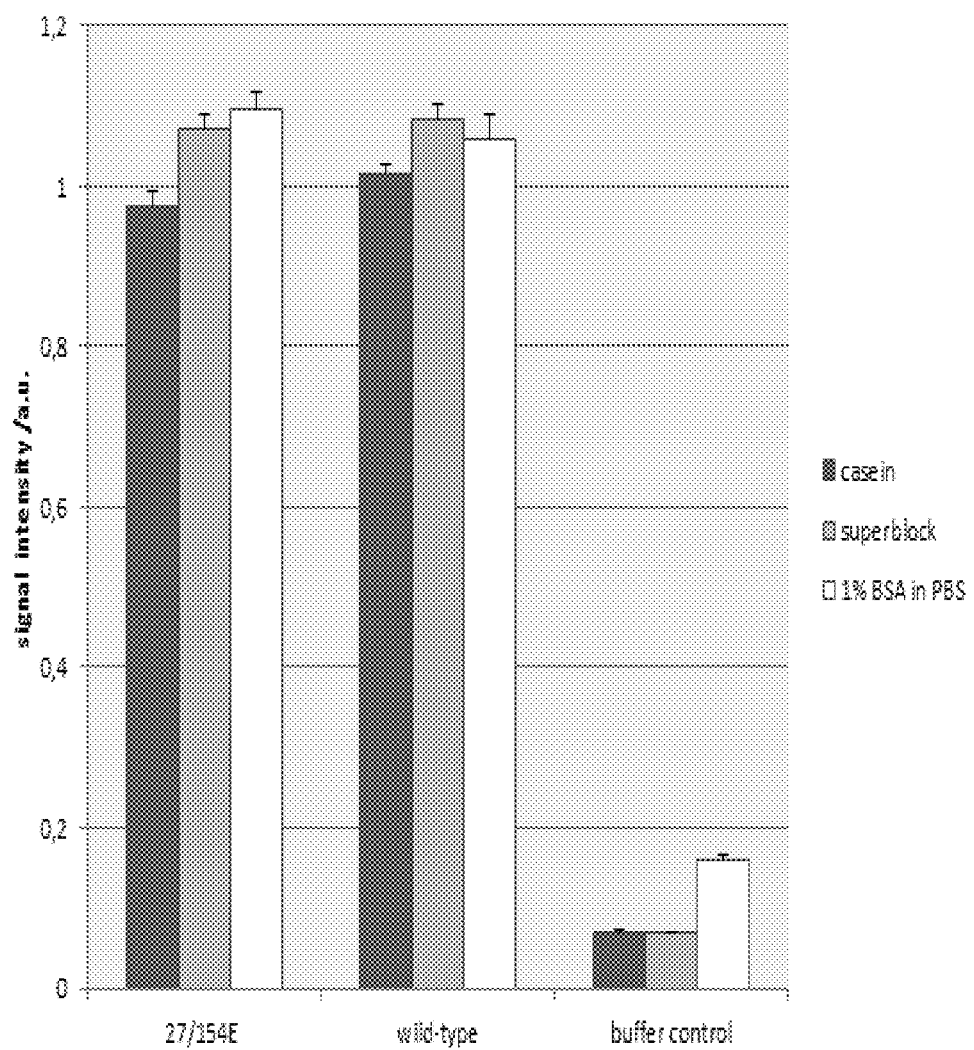
FIG. 5 ELISA plates (Maxisorp, Thermo Fisher Scientific) were coated either with purified denatured MSBI1 Rep wt or mutant MSBI1 Rep 27/154E at 4° C. overnight in 1:1 dilution of 1×PBS/8 M urea (200 ng protein per well) in triplicates. Blocking was performed in different assay buffers (casein, superblock, 1% BSA in PBS) for 2 h at RT. The coated protein was quantified with a pool of three mouse monoclonal anti-Rep antibodies (1:500 dilution, with epitopes in the N-, central-, and C-terminal Rep domain) as primary antibodies followed by incubation with an HRP-coupled goat anti-mouse secondary antibody (1:5000 dilution, each 1 h at 37° C., washing with PBS 0.1% Tween, TMB ELISA substrate from Thermo Fisher Scientific, readout at 450 nm). Raw signal intensities are shown.

Importantly, the newly engineered double Rep mutant shows a comparable ELISA coating performance when compared to the wild-type Rep protein (assay buffers: casein buffer, superblock buffer, 1% BSA in PBS) (FIG. 5).

B. ELISA Performance of Wildtype or Mutant Rep Protein in Human MS Sera

Additionally, the reactivity of Rep-reactive antibodies in human MS sera was increased by about 40% on average when using the 27/154E Rep double mutant as antigen when compared to wild-type Rep in ELISA assays (FIG. 6.)

Example 4

Purification of Wildtype and Mutant Rep Protein Antigen

A nucleotide acid molecule encoding either the full-length wild-type Rep open reading frame (ORF) identified within the MSBI1 genome, or a nucleotide acid molecule Rep double mutant 27/154E are cloned into an expression plasmid (pEXP5-CT, Invitrogen) enabling protein expression in *E. coli*. Briefly, chemically competent *E. coli* (SoluB121, Genlantis) were transfected with the expression plasmid followed by clonal selection on LB-agar plates with ampicillin. High level protein expression clones were selected by protein test expressions in a low volume pre-screening. Therefore clonal cultures were expanded to about 10 ml in LB Amp (37° C., shaking device) until an OD600 of 0.4-0.6 was reached followed by induction of protein expression with isopropyl β-D-1-thiogalactopyranoside (IPTG, 0.66 mM) over night at 25° C. on a shaking device.

The target protein expression was determined by SDS-PAGE and Western Blotting of the *E. coli* lysates (prepared in Lämmli SDS-PAGE sample buffer) with anti-His antibodies reactive against the C-terminal 6×His tag of the Rep protein. The initial *E. coli* culture showing the highest expression of Rep protein was then further expanded to 1000 ml LB Amp, brought to an OD600 of 0.5. Protein expression was induced by IPTG (0.66 mM) over night at 25° C. on a shaking device. Cells were then centrifuged at 6000 g at 4° C., washed with PBS and stored at −80° C. in aliquots (10 aliquots corresponding to each 100 ml of the 1000 ml initial IPTG-induced *E. coli* culture).

The synthesized Rep protein having the amino acid sequence of SEQ ID NO:1 (wildtype) or SEQ ID NO:11 (mutant) within the *E. coli* expression is denaturated by adding 20 reaction volumes 8 M urea sample buffer pH 8.0 containing 100 mM NaH2PO4, 10 mM Tris HCl, pH 8.0, 5 mM imidazole, 5 mM beta-mercaptoethanol. The Rep protein was subsequently purified under denaturing conditions (55 mM imidazole for washing and 300 mM imidazole for protein elution) based on a C-terminal His6-tag fused to the Rep protein. The quality of purification was determined by Coomassie protein staining and Western Blotting with anti-Rep protein antibodies. The Rep protein purity is densitometrically calculated and greater 95%. The purified protein is either directly used for ELISA-based serum screening or subjected to SDS-Page followed by transfer blotting onto nitrocellulose membranes for serum incubation of 1D-size-resolved Rep protein membrane stripes.

```
                        SEQUENCE SUMMARY

SEQ
ID
NO  SEQUENCE

1  Amino acid sequence of Rep protein encoded by MSBI1.176 (wild-
    type)
    MSDLIVKDNALMNASYNLALVEQRLILLAIIEARETGKGINANDPLTVHASSYINQFNVERHT
    AYQALKDACKDLFARQFSYQEKRERGRINITSRWVSQIGYMDDTATVEIIFAPAVVPLITRLE
    EQFTQYDIEQISGLSSAYAVRMYELLICWRSTGKTPIIELDEFRKRIGVLDTEYTRTDNLKMR
    VIELALKQINEHTDITASYEQHKKGRVITGFSFKFKHKKQNSDKTPKNSDSSPRIVKHSQIPT
    NIVKQPENAKMSDLEHRASRVTGEIMRNRLSDRFKQGDESAIDMMKRIQSEIITDAIADQWES
    KLEEFGVVF 2  Amino acid sequence of Rep peptide fragment
    EARETGKGINANDPLTVH 3  Amino acid sequence of Rep peptide fragment
    KQINEHTDITASYEOHKKGRT 4  His-Tag (with two neutral stuffer amino acids)
    GAHHHHHH 5  T7-Tag
    MASMTGGQQMG 6  FLAG-Tag
    DYKDDDDK 7  Strep-II-Tag
    WSHPQFEK 8  Amino acid sequence of Rep protein encoded by MSBI2.176 (wild-
    type)
    MSKLVVKDNALMNASYNLDLVEQRLILLAIIEARESGKGINANDPLTVHAESYINQFGVHRVT
    AYQALKDACDNLFARQFSYQSKSEKGNIQNHRSRWVSEIIYIDTEATVKIIFAPAIVPLITRL
    EEQFTKYDIEQISDLSSAYAIRLYELLICWRSTGKTPIIGLGEFRNRVGVLDSEYHRIAHLKE
    RVIEHSIKQINEHTDITATYEQHKKGRTITGFSFKFKQKKPKQAEIATETPKTATNDPDTTKP
    LTEPQTAKYSMILCKLGSISDLSNFPDYPAFANWIGNILRNPEKADEQTAKRIFTALKTETDY
    SKKN 9  MSBI.1 specific epitope
    NRLSDRF
```

SEQUENCE SUMMARY

| SEQ ID NO | SEQUENCE |
|---|---|
| 10 | Nucleotide sequence of synthesized mutant Rep protein encoding MSBI1 Rep 27/154E (mutant DNA)<br>ATGAGCGACCTGATCGTGAAAGACAATGCCCTGATGAACGCCTCCTACAACCTGGCACTGGTC<br>GAACAGAGACTGATTGAGCTGGCTATCATCGAGGCAAGGGAGACCGGCAAGGGCATCAACGCC<br>AATGACCCCTGACAGTGCACGCCAGCTCCTACATCAACCAGTTTAATGTGGAGCGCCACACC<br>GCCTATCAGGCCCTGAAGGACGCCTGCAAGGATCTGTTTGCCCGGCAGTTCAGCTACCAGGAG<br>AAGCGGGAGAGAGGCAGGATCAACATCACAAGCAGATGGGTGTCCCAGATCGGCTATATGGAC<br>GATACCGCCACAGTGGAGATCATCTTTGCACCAGCAGTGGTGCCTCTGATCACCAGGCTGGAG<br>GAGCAGTTCACACAGTACGACATCGAGCAGATCTCCGGACTGTCTAGCGCCTACGCCGTGCGC<br>ATGTATGAGCTGCTGATCGAGTGGCGGTCTACCGGCAAGACACCTATCATCGAGCTGGATGAG<br>TTCCGCAAGCGGATCGGCGTGCTGGACACCGAGTACACCAGAACAGATAACCTGAAGATGAGA<br>GTGATCGAGCTGGCCCTGAAGCAGATCAATGAGCACACCGATATCACAGCCTCTTATGAGCAG<br>CACAAGAAGGGCCGCGTGATCACCGGCTTCAGCTTTAAGTTCAAGCACAAGAAGCAGAACTCT<br>GACAAGACACCAAAGAATAGCGATTCCTCTCCCCGGATCGTGAAGCACAGCCAGATCCCTACC<br>AACATCGTGAAGCAGCCAGAGAATGCCAAGATGTCCGACCTGGAGCACAGGGCATCTAGGGTG<br>ACAGGCGAGATCATGAGAAATAGGCTGAGCGATCGGTTCAAGCAGGGCGACGAGTCCGCCATC<br>GATATGATGAAGAGAATCCAGTCCGAGATCATCACCGACGCCATCGCCGATCAGTGGGAATCT<br>AAACTGGAAGAGTTTGGAGTCGTGTTTGGAGCACATCACCATCATCATCACTGA |
| 11 | Amino acid sequence of Rep protein encoded by MSBI1 Rep 27/154E (mutant protein)<br>MSDLIVKDNALMNASYNLALVEQRLIELAIIEARETGKGINANDPLTVHASSYINQFNVERHT<br>AYQALKDACKDLFARQFSYQEKRERGRINITSRWVSQIGYMDDTATVEIIFAPAVVPLITRLE<br>EQFTQYDIEQISGLSSAYAVRMYELLIEWRSTGKTPIIELDEFRKRIGVLDTEYTRTDNLKMR<br>VIELALKQINEHTDITASYEQHKKGRVITGFSFKFKHKKQNSDKTPKNSDSSPRIVKHSQIPT<br>NIVKQPENAKMSDLEHRASRVTGEIMRNRLSDRFKQGDESAIDMMKRIQSEIITDAIADQWES<br>KLEEFGVVF |
| 12 | Amino acid sequence of Rep protein encoded by MSBI2 Rep 27/154E (mutant protein)<br>MSKLVVKDNALMNASYNLDLVEQRLIELAIIEARESGKGINANDPLTVHAESYINQFGVHRVT<br>AYQALKDACDNLFARQFSYQSKSEKGNIQNHRSRWVSEIIYIDTEATVKIIFAPAIVPLITRL<br>EEQFTKYDIEQISDLSSAYAIRLYELLIEWRSTGKTPIIGLGEFRNRVGVLDSEYHRIAHLKE<br>RVIEHSIKQINEHTDITATYEQHKKGRTITGFSFKFKQKKPKQAEIATETPKTATNDPDTTKP<br>LTEPQTAKYSMILCKLGSISDLSNFPDYPAFANWIGNILRNPEKADEQIAKRIFTALKTETDY<br>SKKN |

REFERENCES

Funk, M., et al. (2014). "Isolation of protein-associated circular DNA from healthy cattle serum". Genome Announc 2(4)

Giraldo, R., et al. (2011). "RepA-WH1 prionoid: a synthetic amyloid proteinopathy in a minimalist host." Prion 5(2): 60-64

Giraldo, R. (2007). "Defined DNA sequences promote the assembly of a bacterial protein into distinct amyloid nanostructures." Proc Natl Acad Sci USA 104(44): 17388-17393.

Gunst, K., et al. (2014). "Isolation of bacterial plasmid-related replication-associated cirular DNA from a serum sample of a multiple sclerosis patient." Genome Announc 2(4).

Lamberto, I., et al. (2014). "Mycovirus-like DNA virus sequences from cattle serum and human brain and serum samples from multiple sclerosis patients." Genome Announc 2(4).

Linding, R., J. Schymkowitz, F. Rousseau, F. Diella and L. Serrano (2004). "A comparative study of the relationship between protein structure and beta-aggregation in globular and intrinsically disordered proteins." J Mol Biol 342(1): 345-353.

Manuelidis L., 2011. "Nuclease resistant circular DNAs co-purify with infectivity in scrapie and CJD". J. Neurovirol. 17:131-145.

Rousseau, F., J. Schymkowitz and L. Serrano (2006). "Protein aggregation and amyloidosis: confusion of the kinds?" Curr Opin Struct Biol 16(1): 118-126.

Torreira, E., et al. (2015). "Amyloidogenesis of bacterial prionoid RepA-WH1 recaptiulates dimer to monomer transitions of RepA in DNA replication initiation." Structure 23(1):183-189

Whitley, C., et al. (2014). "Novel replication-competent cirulara DNA molecules from healthy cattle serum and milk and multiple sclerosis-affected human brain tissue." Genome Announc 2(4).

The invention claimed is:

1. A DNA-replication-associated (Rep) protein comprising the amino acid sequence of SEQ ID NOs: 11 or 12.

2. A method of diagnosing multiple sclerosis (MS) in a subject comprising the steps of
   (a) incubating a sample from a subject with a Rep protein as defined in claim 1;
   (b) detecting the amount of antibodies in the sample from the subject forming an immunological complex with the Rep protein; and
   (c) correlating the amount of antibody bound to Rep protein in the sample from the subject, as compared to an amount in a control sample, for diagnosing MS.

3. The method of claim 2, wherein in step (a) the Rep protein is immobilized followed by incubating the immobilized Rep protein with the sample from the subject.

4. The method of claim 2, wherein in step (a) the Rep protein is expressed in cells followed by incubating the cells with the sample from the subject.

5. The method of claim 2, wherein in step (b) the amount of antibodies forming an immunological complex with Rep protein is quantified by a detecting binding agent coupled to a signal generating compound.

6. The method of claim 2, wherein in step (a), the antibodies in the sample from the subject are immobilized prior to incubating with a defined amount of the Rep protein.

7. The method of claim 2, wherein the sample from the subject is a serum or a plasma sample.

8. The method of claim 2, wherein MS or a predisposition for MS is indicated by an increased amount of anti-Rep antibodies in the subject's sample of at least 2 fold as compared to a control sample.

9. A kit for use in the diagnosis of MS comprising:
   (a) a Rep protein, wherein the Rep protein comprises the amino acid sequence of SEQ ID NO:11 or 12;
   (b) an anti-human antibody coupled to a detectable label and capable of binding to anti-Rep antibody with a specificity for a protein having the amino acid sequence of SEQ ID NO: 11 or 12, and
   (c) a solid matrix suitable for immobilizing a Rep protein according to (a).

10. The kit according to claim 9 for use in an assay selected from the group consisting of enzyme-linked immunosorbent assay (ELISA), radioimmunoassay (RIA), enzyme immune assay (EIA), fluorescence immunoassay (FIA), luminescence immunoassay (LIA) and strip assay.

* * * * *